United States Patent
Kmiec, Jr.

(10) Patent No.: US 11,701,132 B2
(45) Date of Patent: Jul. 18, 2023

(54) LATERAL CORTEX PENETRATOR

(71) Applicant: Depuy Synthes Products, Inc., Raynham, MA (US)

(72) Inventor: Stanley J. Kmiec, Jr., Morgantown, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 61 days.

(21) Appl. No.: 17/212,600

(22) Filed: Mar. 25, 2021

(65) Prior Publication Data
US 2022/0304709 A1    Sep. 29, 2022

(51) Int. Cl.
| A61B 17/17 | (2006.01) |
| A61B 17/16 | (2006.01) |
| A61B 17/34 | (2006.01) |
| A61B 17/56 | (2006.01) |

(52) U.S. Cl.
CPC ...... *A61B 17/1721* (2013.01); *A61B 17/1604* (2013.01); *A61B 17/1615* (2013.01); *A61B 17/1633* (2013.01); *A61B 17/1668* (2013.01); *A61B 17/1697* (2013.01); *A61B 17/1725* (2013.01); *A61B 17/1753* (2013.01); *A61B 17/3472* (2013.01); *A61B 2017/564* (2013.01)

(58) Field of Classification Search
CPC . A61B 17/16; A61B 17/1604; A61B 17/1613; A61B 17/1615; A61B 17/1633; A61B 17/1635; A61B 17/1637; A61B 17/1697; A61B 17/17; A61B 17/175; A61B 17/1753; A61B 2017/564; A61B 17/1668; A61B 17/1721; A61B 17/3472
See application file for complete search history.

(56) References Cited

U.S. PATENT DOCUMENTS

| 4,696,308 | A  | 9/1987  | Meller |
| 4,860,735 | A  | 8/1989  | Davey et al. |
| 6,835,197 | B2 | 12/2004 | Roth et al. |
| 7,175,633 | B2 | 2/2007  | Roth et al. |
| 7,306,600 | B2 | 12/2007 | Roth et al. |

(Continued)

FOREIGN PATENT DOCUMENTS

| WO | 2005096952 A1 | 10/2005 |
| WO | 2006060416 A2 | 6/2006 |
| WO | 2007054591 A1 | 5/2007 |

OTHER PUBLICATIONS

International Search Report and Written Opinion for PCT/IB2022/052435 dated May 23, 2022.

*Primary Examiner* — Larry E Waggle, Jr.
(74) *Attorney, Agent, or Firm* — Kramer & Amado, P.C.

(57) ABSTRACT

A system for penetrating the lateral cortex of a long bone includes a tubular cortex penetrator having an inner surface and an outer surface, a proximal end, and a distal end comprising a beveled cutting edge configured to penetrate the lateral cortex. A guide wire is configured to pass over the tubular cortex penetrator, and a guide sleeve is configured to surround the outer surface of the tubular cortex penetrator. A hollow extraction screw with an axial bore, a proximal end, a distal end, and a threaded cutting edge is configured to pass through the axial bore of the hollow extraction screw; and the hollow extraction screw is configured to retract into a distal end of a bore through the tubular cortex penetrator.

15 Claims, 8 Drawing Sheets

(56) References Cited

U.S. PATENT DOCUMENTS

| | | | |
|---|---|---|---|
| 7,918,853 B2 * | 4/2011 | Watanabe | A61B 17/1668 |
| | | | 606/65 |
| 8,025,666 B2 | 9/2011 | Roth et al. | |
| 8,221,423 B2 * | 7/2012 | Gil | A61B 17/1635 |
| | | | 606/180 |
| 8,551,093 B2 | 10/2013 | Roth et al. | |
| 8,808,293 B2 | 8/2014 | Buettler et al. | |
| 8,821,378 B2 * | 9/2014 | Morgenstern Lopez | |
| | | | A61B 17/1671 |
| | | | 600/107 |
| 9,101,432 B2 | 8/2015 | Limouze et al. | |
| 9,155,582 B2 | 10/2015 | Felder et al. | |
| 9,381,054 B2 | 7/2016 | Felder et al. | |
| 9,427,266 B2 | 8/2016 | Kmiec, Jr. | |
| 9,918,757 B2 | 3/2018 | Roth et al. | |
| 10,271,881 B2 | 4/2019 | Roth et al. | |
| 10,517,608 B2 * | 12/2019 | Jenkins | A61B 17/24 |
| 2007/0270711 A1 | 11/2007 | Gil | |
| 2019/0380752 A1 | 12/2019 | Ferrero Manzanal et al. | |

* cited by examiner

LATERAL CORTEX PENETRATOR

TECHNICAL FIELD

Various embodiments disclosed herein relate generally to tools for penetrating the lateral cortex of a long bone. Disclosed embodiments further relate to penetrating the lateral cortex of a long bone to facilitate introduction of devices into the interior of a long bone.

BACKGROUND

Fractures of the femur at or near the hip may require repair through surgical intervention. In some cases, a compression hip screw or helical blade device including a screw, pin, blade, or nail may be used. The screw, pin, blade, or nail is inserted into a premade tapped drill hole in the femoral neck and head, and an angled side plate is placed over the distal end of the screw and fixed with screws to the proximal femoral shaft. The side plate provides a stable attachment of the screw, pin, or nail through the neck of the femur to the shaft of the bone.

Intertrochanteric fractures at the hip may be repaired with intramedullary nails or pins through the shaft of the femur. One commonly used technique involved insertion of thin-diameter solid nails (Enders nails) from the knee toward the hip, in a retrograde fashion. This technique has been abandoned, as it allowed excessive external rotation of the bone and knee pain.

Antegrade nails inserted through the greater trochanter are now more frequently used. The nail is inserted along the shaft of the femur toward the knee. To prevent rotation of the nail, a head element, which may be a lag screw or helical blade, is inserted through a hole formed obliquely through the proximal portion of the nail into the femoral head. The lag screw enters the bone through an opening created in the lateral cortex of the femur using a drill.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

In view of the foregoing, it would be desirable to have improved tools for penetrating the lateral cortex of a long bone to insert a lag screw or helical blade through an intramedullary nail. In particular, it would be desirable to have tools with cutting edges configured to penetrate the lateral cortex of a long bone, with a reduced likelihood of damaging an intramedullary nail.

Various embodiments disclosed herein relate to a system for penetrating the lateral cortex of a bone, including a guide wire; a tubular cortex penetrator having an inner surface, an outer surface, and an axial bore therethrough configured to pass over the guide wire; and a hollow extraction screw with an axial bore, a proximal end, a distal end, and a threaded first cutting edge on the outer surface of the hollow extraction screw. The tubular cortex penetrator includes a proximal end, and a distal end comprising a beveled cutting edge configured to penetrate the lateral cortex. The guide wire is configured to pass through the axial bore of the hollow extraction screw; and the hollow extraction screw is configured to retract into a distal end of the axial bore of the tubular cortex penetrator.

The system may further include a guide sleeve for a lag screw or helical blade, where the guide sleeve is configured to surround the outer surface of the tubular cortex penetrator.

In various embodiments, at least a portion of the inner surface of the tubular cortex penetrator is constricted so as to prevent radial movement of the hollow extraction screw within the tubular cortex penetrator, while allowing axial movement of the hollow extraction screw.

The proximal end of the tubular cortex penetrator may be configured to receive an impact from a tool, and the cutting edge at the distal end of the tubular cortex penetrator may be configured to penetrate the lateral cortex upon transmission of an impact force from the proximal end.

The tubular cortex penetrator may be configured to be rotated about an axis thereof, and the cutting edge at the distal end of the tubular cortex penetrator may be is configured to cut through the lateral cortex upon rotation of the tubular cortex penetrator.

In various embodiments, the tubular cortex penetrator includes a proximal end, and a distal end comprising a beveled cutting edge configured to penetrate the lateral cortex, where the cutting edge at the distal end of the tubular cortex penetrator is on the outer surface of the tubular cortex penetrator, and the inner surface of the tubular cortex penetrator is beveled. Alternatively, the cutting edge at the distal end of the tubular cortex penetrator is on the inner surface of the tubular cortex penetrator, and the outer surface of the tubular cortex penetrator is beveled.

Various embodiments disclosed herein relate to a system for penetrating the lateral cortex of a bone, including a guide wire; a tubular cortex penetrator having an inner surface, an outer surface, and an axial bore therethrough configured to pass over the guide wire; and a hollow extraction screw with an axial bore, and a threaded first cutting edge on the outer surface of the hollow extraction screw. The outer surface of the hollow extraction screw may include a second cutting edge comprising at least one flute at the distal tip of the hollow extraction screw; and the threaded first cutting may be proximal to the second cutting edge. Alternatively, the hollow extraction screw may include the threaded first cutting edge at the distal tip of the hollow extraction screw.

Various embodiments relate to a method of penetrating the lateral cortex using a system including a guide wire; a tubular cortex penetrator having an inner surface, an outer surface, and an axial bore therethrough configured to pass over the guide wire; and a hollow extraction screw with an axial bore, a proximal end, a distal end, and a threaded first cutting edge on the outer surface of the hollow extraction screw. The method includes:

advancing a guide wire to a surgical site through the lateral cortex and into the femoral neck and femoral head;

passing the hollow extraction screw over the guide wire to the surgical site;

introducing the tubular cortex penetrator to the surgical site by passing the tubular cortex penetrator distally over the hollow extraction screw;

drilling the hollow extraction screw into the lateral cortex; and using the cutting edge at the distal end of the tubular cortex penetrator to cut a hole through the lateral cortex to form a disk of severed bone. The hollow extraction screw, the tubular cortex penetrator, and the disk of severed bone may then be withdrawn from the surgical site while leaving the guide wire in position.

The method of penetrating the lateral cortex, may further include introducing a guide sleeve to the surgical site; and introducing the tubular cortex penetrator to the surgical site through the guide sleeve.

Various embodiments disclosed herein relate to a system for perforating the cortical surface of a bone and extracting bone material from the interior of said bone to thereby create a passageway into the interior of the bone, including:

an exterior tubular member having an interior passage and a longitudinal axis having a distal and proximal end, the tubular member comprising a tapered cutting edge at its distal end configured to be advanced at least partially through the exterior surface of a bone;

an extraction screw configured to be inserted through the interior passage of the outer tubular member and into the interior of a bone to assist in extracting bone material, the extraction screw including an interior passage and a longitudinal axis having a distal and proximal end, the distal end including a tapered tip and a plurality of threaded protrusions proximal to the tapered distal end; and a guide wire over which the extraction screw is advanceable.

Various embodiments disclosed herein relate to a system for penetrating the lateral cortex, including:

a guide wire;

a tubular cortex penetrator having an inner surface configured to pass over the guide wire and an outer surface, the tubular cortex penetrator including a proximal end, and a distal end comprising a beveled cutting edge configured to penetrate the lateral cortex; and a guide sleeve configured to surround the outer surface of the tubular cortex penetrator.

The guide wire may be configured to pass through the axial bore of the hollow extraction screw; and at least a portion of the inner surface of the tubular cortex penetrator may be constricted so as to prevent radial movement of the hollow extraction screw within the tubular cortex penetrator, while allowing axial movement of the guide wire. The tubular cortex penetrator may be configured to be rotated about an axis thereof, and the cutting edge at the distal end of the tubular cortex penetrator may be configured to cut through the lateral cortex upon rotation of the tubular cortex penetrator. The cutting edge at the distal end of the tubular cortex penetrator may be on the outer surface of the tubular cortex penetrator, and the inner surface of the tubular cortex penetrator may be beveled.

Various embodiments disclosed herein relate to a method for penetrating the lateral cortex with a system including a guide wire; a tubular cortex penetrator having an inner surface configured to pass over the guide wire and an outer surface, the tubular cortex penetrator including a proximal end, and a distal end comprising a beveled cutting edge configured to penetrate the lateral cortex; and a guide sleeve configured to surround the outer surface of the tubular cortex penetrator. The method includes steps of:

introducing the guide sleeve to a surgical site near the lateral cortex;

introducing the guide wire to the surgical site through the guide sleeve;

passing the tubular cortex penetrator through the guide sleeve over the guide wire, so that the cutting edge at the distal end of the tubular cortex penetrator exits the guide sleeve near the lateral cortex;

using the cutting edge of the tubular cortex penetrator to penetrate the lateral cortex; and withdrawing the tubular cortex penetrator, while leaving the guide wire and guide sleeve in position.

BRIEF DESCRIPTION OF THE DRAWINGS

In order to better understand various exemplary embodiments, reference is made to the accompanying drawings, wherein.

DETAILED DESCRIPTION

Referring now to the drawings, in which like numerals refer to like components or steps, there are disclosed broad aspects of various exemplary embodiments.

The current disclosure is directed to improved methods of repairing a broken femur, which allow a lag screw to be inserted through a an intermedullary nail without damaging the nail. Antegrade nails inserted through the greater trochanter are frequently used to repair a broken femur. The nail is inserted along the shaft of the femur toward the knee. To prevent rotation of the nail, the lag screw is inserted through a hole formed obliquely through the proximal portion of the nail into the femoral head. The lag screw enters the bone through an opening created in the lateral cortex of the femur using a drill. However, in numerous cases, the drill strikes the oblique hole in the nail and damages the nail. This damage creates a notch in the nail near the oblique hole, where the nail is weakest. This may lead to decreased strength and reduce the life of the intramedullary nail. In some cases, surgery to replace a damaged nail with a new nail may be required.

Figure 1:
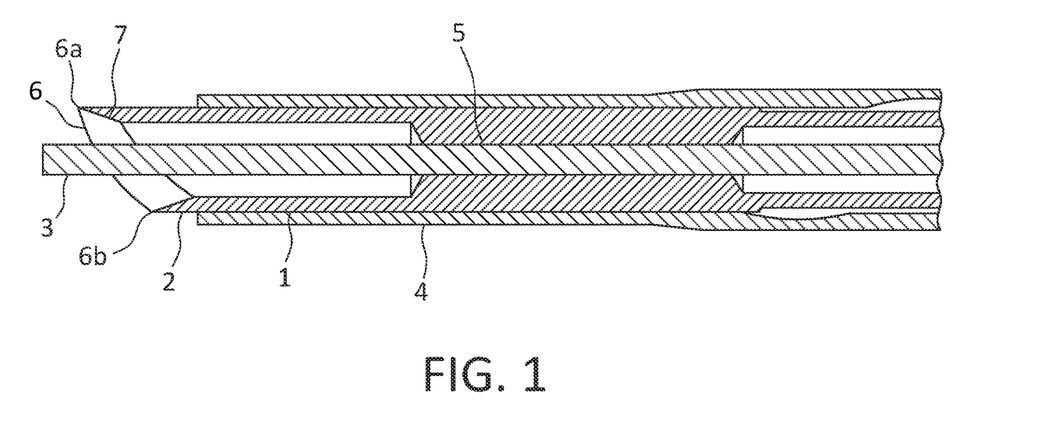
FIGS. 1 and 2 illustrate a first embodiment of a system for penetrating the lateral cortex of a long bone, including a tubular cortex penetrator.

FIG. 1 shows a cross section view of a first embodiment of a system for penetrating the lateral cortex of a long bone. The system of FIG. 1 includes a tubular cortex penetrator 1 having an inner surface and an outer surface. Tubular cortex penetrator 1 includes a proximal end, and a distal end 2 including a cutting edge 6 configured to penetrate the lateral cortex. The cutting edge is formed by at least one beveled surface 7 on distal end 2. In various embodiments, the cutting edge 6 is formed at the outer surface of tubular cortex penetrator 1 by a beveled surface 7 which is sloped from the inner surface to tubular cortex penetrator 1 to its outer surface. Alternatively, the cutting edge 6 is formed at the inner surface of tubular cortex penetrator 1 by a beveled surface 7 which is sloped from the outer surface of tubular cortex penetrator 1 to its inner surface. Also, the cutting edge 6 may be formed by two beveled surfaces 7 on tubular cortex penetrator 1, where one beveled surface 7 is formed on an outer surface of penetrator 1, and the other beveled surface 7 is formed on an inner surface of penetrator 1. The system of FIG. 1 additionally includes a guide wire 3 configured to pass through a bore of tubular cortex penetrator 1 and a tubular blade/screw guide sleeve 4 (guide sleeve) configured to surround the outer surface of the tubular cortex penetrator. The cutting edge 6 of penetrator 1 may be exposed at one end of the guide sleeve. A thickened inner wall 5 near the distal end of tubular cortex penetrator 1 prevents radial movement of guide wire 3 within tubular cortex penetrator 1. Upon removal of penetrator 1 from guide sleeve 1, a head element, i.e., a lag screw or a helical blade, may be advanced into the femoral head through the guide sleeve. Guide sleeve 4 protects soft tissue from damage by sharp surfaces on the lag screw or helical blade.

In some embodiments, the cutting edge 6 of tubular cortex penetrator 1 is angled relative to an axis of tubular cortex penetrator 1. As shown in FIG. 1, cutting edge 6 may be a variable distance from the proximal end of penetrator 1, with the cutting edge 6 extending the greatest distance from the proximal end of penetrator 1 at a first point 6a and the shortest distance from the proximal end of penetrator 1 at a second point 6b, where the first point 6a and the second point 6b are 180° from each other about a peripheral surface of penetrator 1. The first point 6a, the second point 6b, and cutting edge 6 may define a curved surface, as shown in FIG. 1. The first point 6a, the second point 6b, and cutting edge 6 may define a planar surface, where the axis of penetrator 5 intersects the planar surface at an angle of 30° to 90°, 40° to 80°, 40° to 75°, 45° to 75°, or 45° to 60°.

Between the proximal end of penetrator 1 and the distal end of penetrator 1, a thickened inner wall 5 of penetrator 1 has a narrow bore with a first diameter which allows the guide wire 3 to pass therethrough, while preventing radial motion of the guide wire 3 as it passes through inner wall 5. At the proximal end of penetrator 1, penetrator 1 has an enlarged bore with a second diameter, where the bore having the second diameter allows tissue removed as the cutting edge 6 penetrates the lateral cortex to enter the distal end of penetrator 1, entering a space between guide wire 3 and the inner surface of penetrator 1. The bore of the penetrator 1 at the distal end may have a diameter ranging from the second diameter, as shown in FIG. 1, to the first diameter.

Figure 2:
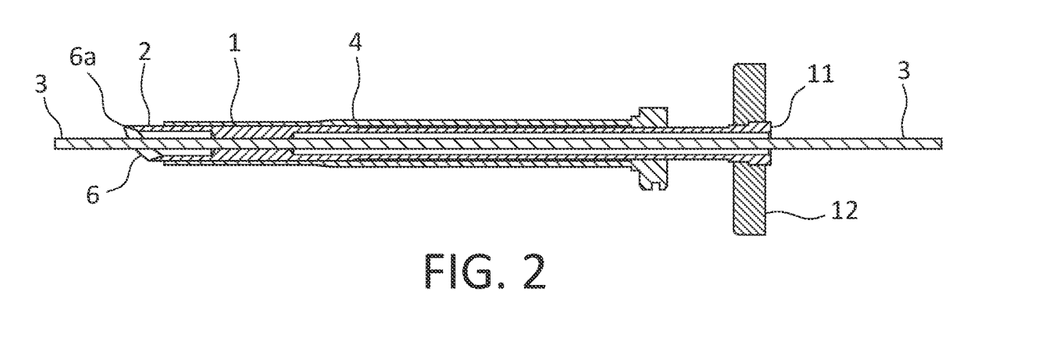

FIG. 2 shows a second cross section view of the first embodiment of FIG. 1. As seen in FIG. 2, tubular cortex penetrator 1 includes an expanded proximal end 11, where proximal end 11 may be expanded in a stepwise fashion, as shown in FIG. 2, or in a tapered fashion. A handle 12 is fitted to proximal end 11 of penetrator 1. In various embodiments, handle 12 is welded to proximal end 11 of penetrator 1. Handle 12 has at least one directional feature, represented by an arrow in FIG. 2, which is oriented so as align with point 6a at the distal end of penetrator 1.

Figure 3:
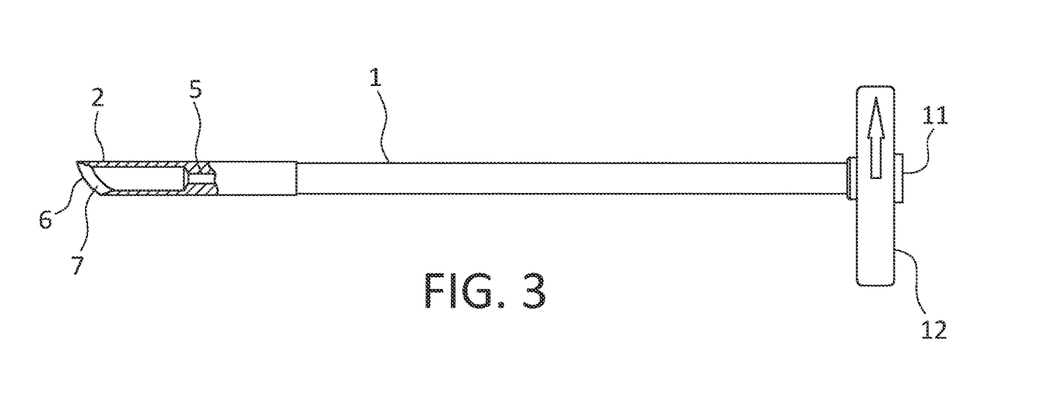
FIGS. 3 and 4 illustrates two views of a tubular cortex penetrator for use in the system of FIGS. 1 and 2.

FIG. 3 shows a cutaway view of tubular penetrator 1, as seen in the embodiment of FIG. 1. As seen in FIG. 3, tubular penetrator 1 may include a distal end 2 with a cutting edge 6 at the outer surface of penetrator 1, where the cutting edge 6 is formed by a beveled inner surface 7. Tubular penetrator 1 includes a bore configured to allow guide wire 3, shown in FIG. 1, to pass therethrough. As seen in FIG. 3, tubular penetrator 1 includes generally narrow walls, except for the thickened inner wall 5. Thickened inner wall 5 allows guide wire 3 to pass therethrough, without allowing radial movement of guide wire 3. The thinner inner wall at distal end 2 allows tissue removed by cutting edge 6, e.g., bone fragments, to enter the space between the guide wire and the inner surface of the penetrator wall at end 2.

Figure 4:
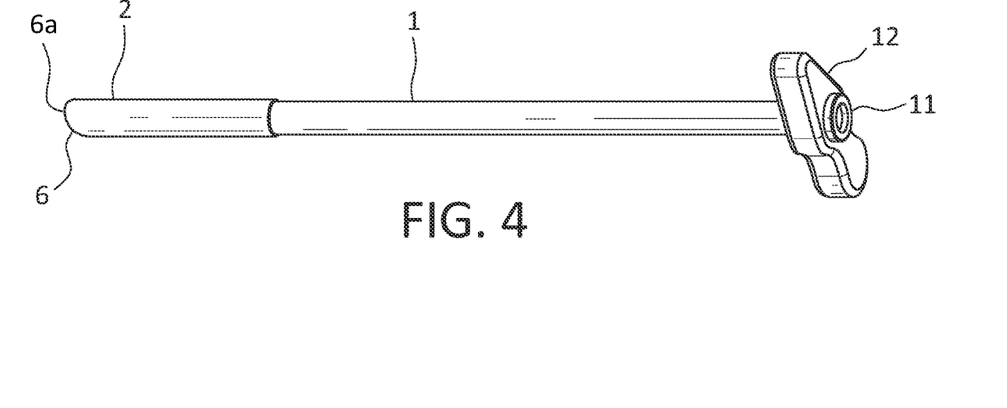

FIG. 4 shows a perspective view of tubular penetrator 1, where handle 12 at the proximal end of penetrator 1 has an arrowhead shape. The pointed end of the arrowhead-shaped handle 12 aligns with the first point 6a on cutting edge 6 at the distal end of penetrator 1. In use, the penetrator is placed against the lateral cortex of a long bone, and is used to penetrate the lateral cortex. The proximal end 11 of the tubular cortex penetrator 1 may be configured to receive an impact from a tool, and the cutting edge 6 at the distal end 2 of the penetrator 1 is configured to penetrate the lateral cortex upon transmission of an impact force from the proximal end. Alternatively, the tubular cortex penetrator is configured to be rotated about its axis, and the cutting edge at the distal end of the tubular cortex penetrator is configured to cut through the lateral cortex upon rotation of the tubular cortex penetrator. The arrowhead-shaped handle 12 may be rotated 360° about an axis of penetrator 1. A single rotation or multiple rotations may be used. Penetrator 1 may be rotated about its axis until the lateral cortex bone is completely cut through. In some embodiments, penetrator 1 is rotated about its axis until the bone of the lateral cortex is scored to a desired depth, and the bone may be fractured along the score by application of force along an axis of penetrator 1.

The handle 12 at the proximal end of penetrator 1 may take a variety of forms, as long as the position of the first point 6a on cutting edge 6 may be determined relative to handle 12. Handle 12 may be shaped as an isosceles triangle, with the triangle having a tip aligned with first point 6a. Handle 12 may be round, oval, square, or rectangular, with a notch, ridge, or color-coded feature being aligned with first point 6a.

Figure 5:
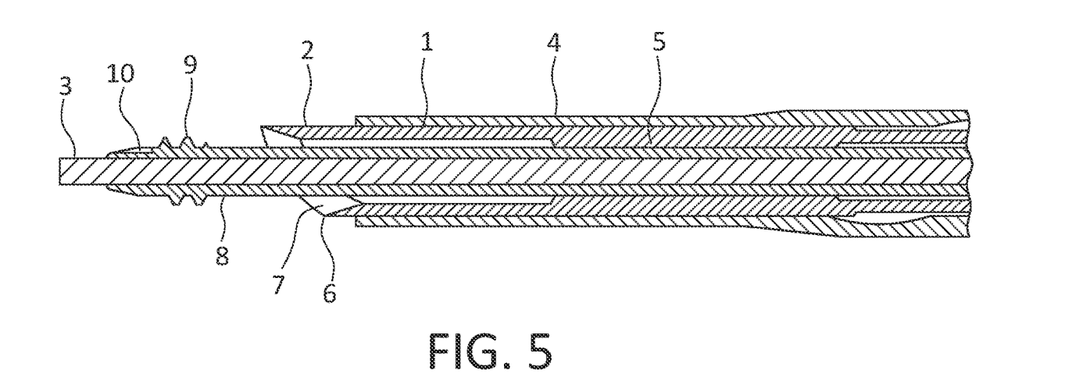
FIGS. 5 and 6 illustrate a second embodiment of a system for penetrating the lateral cortex of a long bone, including a tubular cortex penetrator and a hollow extraction screw.
Figure 6:
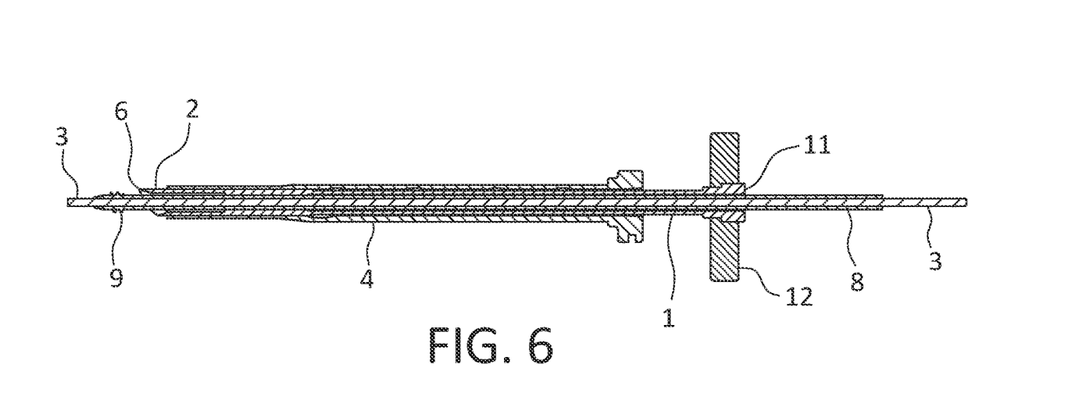

FIGS. 5 and 6 show cross section views of a second embodiment of a system for penetrating the lateral cortex of a long bone. The system of FIGS. 5 and 6 includes a tubular cortex penetrator 1, with a proximal end, and a distal end 2 comprising a cutting edge 6 configured to penetrate the lateral cortex. The cutting edge 6 is formed by at least one beveled surface 7 on distal end 2, where beveled surface 7 may be sloped from the inner surface of tubular cortex penetrator 1 to the outer surface of penetrator 1 or from the outer surface of penetrator 1 to its inner surface. Cutting edge 6 may also be formed by two beveled surfaces 7 on opposite surfaces of tubular cortex penetrator 1. The system of FIG. 5 additionally includes:

a hollow extraction screw 8 with an axial bore, a proximal end, a distal end, and a threaded cutting edge 9 on the outer surface of hollow extraction screw 8;

a guide wire 3 configured to pass through a bore of hollow extraction screw 8; and a tubular guide sleeve 4 configured to surround the outer surface of the tubular cortex penetrator 1.

Figure 7:
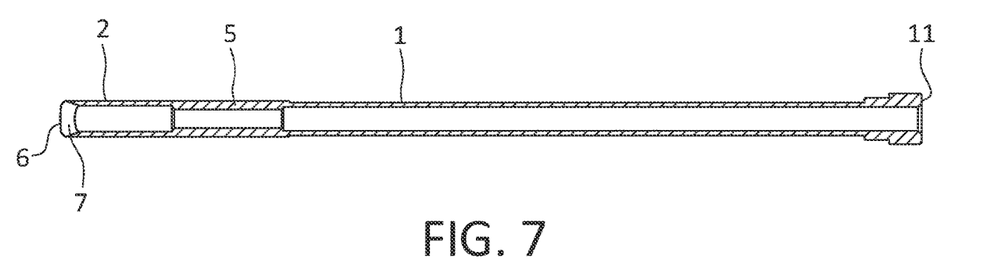
FIG. 7 illustrates a view of a tubular cortex penetrator for use in the system of FIGS. 5 and 6.

The extraction screw 8 in the embodiment of FIG. 5, with the guide wire 3 therein, passes through a bore of tubular cortex penetrator 1. The cutting edge 6 of penetrator 1 in the embodiment of FIG. 5 may be exposed at one end of the guide sleeve. A thickened inner wall 5 near the distal end of tubular cortex penetrator 1 has a bore which is large enough to allow screw 8 to pass therethrough, but narrow enough to prevent radial movement of either the extraction screw 8, or guide wire 3 within the bore of screw 8, within tubular cortex penetrator 1. Comparing FIG. 1 and FIG. 5, the thickened inner wall 5 of the embodiment of FIG. 1 may be thicker than the thickened inner wall 5 of the embodiment of FIG. 5. The thicker wall 5 in the embodiment of FIG. 1 allows guide wire 3 to pass through a narrow bore defined by wall 5. The embodiment of FIG. 5 includes a thinner wall 5 with a larger bore passing therethrough, where the larger bore through wall 5 allows both guidewire 3 and extraction screw 8 to pass therethrough. FIG. 7 shows a cross section view of the isolated tubular cortex penetrator 1.

Figure 8:
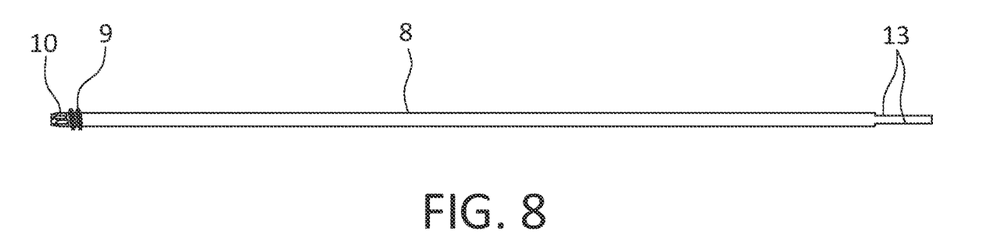
FIG. 8 illustrates a hollow extraction screw for use in the system of FIGS. 5 and 6.

In various embodiments, the hollow extraction screw 8, shown in FIG. 8, has an axial bore, a proximal end, a distal end, and a threaded cutting edge 9 on the outer surface of the extraction screw 8, where threaded cutting edge 9 is at or near the distal tip of screw 8. The outer surface of the hollow extraction screw may have a nonthreaded cutting edge 10, e.g., a cutting edge 10 comprising from one to four cutting edges or flutes spaced about the circumference of hollow extraction screw 8, at the distal tip of the hollow extraction screw 8. Screw 8 may also have a threaded cutting edge 9 on the hollow extraction screw, proximal to the nonhelical cutting edge. The hollow extraction screw 8 may have a proximal end with from two to four planar surfaces configured to be gripped by the chuck arms of a drill or other tool for rotating the hollow extraction screw 8. Alternatively, the outer surface of the hollow extraction screw 8 may have a threaded cutting edge extending to the distal tip of the thread, where the threaded cutting edge may be interrupted by grooves or flutes to enhance cutting.

Figure 9:
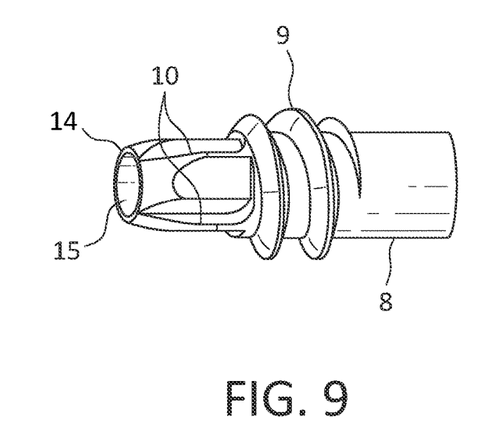
FIGS. 9 and 11 show two embodiments of the cutting surfaces at the distal tip of the hollow extraction screw for use in the system of FIGS. 5 and 6.

FIG. 9 shows a first embodiment of the distal tip of the hollow extraction screw 8. The screw 8 has a hollow bore 15, with a tip 14 formed at the peripheral edge of bore 15 as a wall of hollow extraction screw 8 tapers toward the distal end of the thread. In some embodiments, tip 14 may be sharpened to aid in cutting or scoring of a bone surface. As the wall of hollow extraction screw 8 tapers toward tip 14, from one to four gaps may be cut into the surface of the tapering wall, defining a set of flutes with cutting edges 10. When hollow extraction screw 8 is brought into contact with lateral cortex bone, tip 14 may be used to score the bone surface, and then the cutting edges 10 may be used to cut or carve a hole through the lateral cortex.

Figure 10:
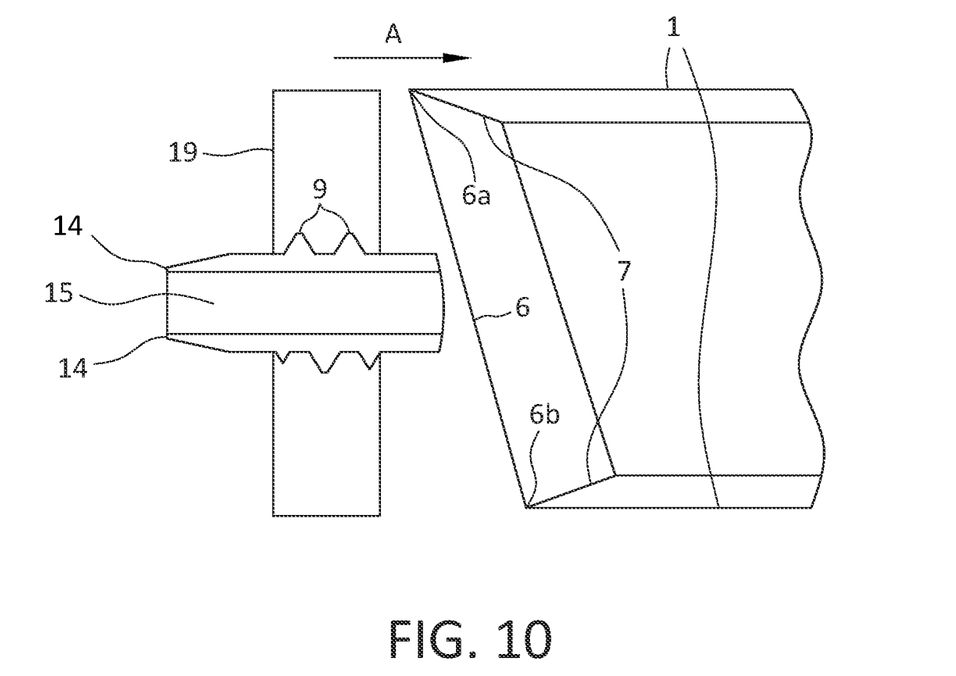
FIG. 10 shows removal of a disc of cortical bone with the system of FIGS. 5 and 6.

Immediately proximal to cutting edges 10, a helical cutting edge 9 is formed as a threading on hollow extraction screw 8. In use, after cutting edges 10 cut a hole through the lateral cortex, helical cutting edge 9 is used to cut into the inner surface of the hole through the lateral cortex. The tubular cortex penetrator 1 is used to cut through the lateral cortex, as described above, after the helical cutting edge 9 cuts into the lateral cortex. The tubular cortex penetrator 1 thus forms a disk 19 of lateral cortex bone, with the disk 19 having a hole therethrough, as shown in FIG. 10.

The helical cutting edge 9 may be partially advanced through the lateral cortex, so that at least a portion of the threading 9 is anchored in a wall of the disk 19 of lateral cortex bone. The tubular cortex penetrator 1 and hollow extraction screw 8 may then be withdrawn in the direction of arrow A. As the hollow extraction screw 8 is withdrawn, the disk of lateral cortex bone is removed from the patient's body. Hollow extraction screw 8 and penetrator 1 are withdrawn without removing guidewire 3 (not shown in FIG. 10), where guidewire 3 is positioned in bore 15 of hollow extraction screw 8.

Alternatively, the helical cutting edge 9 may be fully advanced through the lateral cortex, so that the threading 9 is positioned within cancellous bone and a non-threaded portion of hollow extraction screw 8 passes through a hole in the cortical bone formed by screw 8. The tubular cortex penetrator 1 and hollow extraction screw 8 may then be withdrawn in the direction of arrow A. As the hollow extraction screw 8 is withdrawn, a proximal end of threading 9 is buttressed against an inner surface of disk 19, allowing the user to use hollow extraction screw 8 to pull the disk 19 of lateral cortex bone from the patient's body. Again, hollow extraction screw 8 and penetrator 1 are withdrawn without removing guidewire 3.

Figure 11:
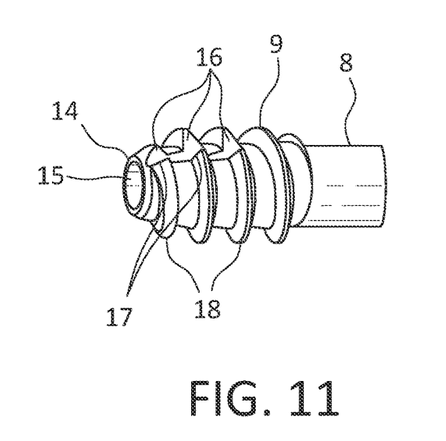

FIG. 11 shows a second embodiment of the distal tip of the hollow extraction screw 8. The embodiment of FIG. 11 has a hollow bore 15, with a tip 14 formed as the wall of hollow extraction screw 8 tapers toward the distal end of the thread. Tip 14 may be sharpened to aid in cutting or scoring of a bone surface. A helical cutting edge 9 is formed as a threading on hollow extraction screw 8. At least a portion of the threads 18 on helical cutting edge 9 are formed at the tapered tip of hollow extraction screw 8, and are interrupted by gaps 16, with each gap forming a flute with a cutting edge 17 in the thread. From one to four gaps may be cut into threads 18. In various embodiments, multiple gaps are cut into threads 15, where the gaps are evenly spaced about the surface of thread 8. Threads 18 may include a single gap, two gaps 180° apart, three gaps 120° apart, or four gaps 90° apart about an axis of thread 8. Gaps 16 may be formed in each thread 18 of helical cutting edge 9. Alternatively, distal threads 18 of helical cutting edge 9 may be formed with gaps on a tapering distal end of hollow extraction screw 8, while proximal threads 18 of helical cutting edge 9 may be formed without gaps or flutes on a portion of hollow extraction screw 8 having a constant diameter. When hollow extraction screw 8 is brought into contact with lateral cortex bone,
    the tip 14 may be used to score the bone surface,
       the cutting edges 17 on threads 18 may be used to cut or carve a hole through the lateral cortex, and
       helical cutting edge 9 is used to cut into the inner surface of the hole through the lateral cortex.

In embodiments where helical cutting edge 9 includes distal threads 18 formed with gaps or flutes 16 and proximal threads 18 formed without gaps or flutes, the distal threads are primarily used to cut the hole through the lateral cortex, while proximal threads 18 are primarily used to cut into the inner surface of the hole in the lateral cortex. The hollow extraction screw of FIG. 9 and the hollow extraction screw of FIG. 11 may each be used to engage and withdraw a disk of lateral cortex bone cut from the bone from a patient's body, generally as shown in FIG. 10.

Figure 12:
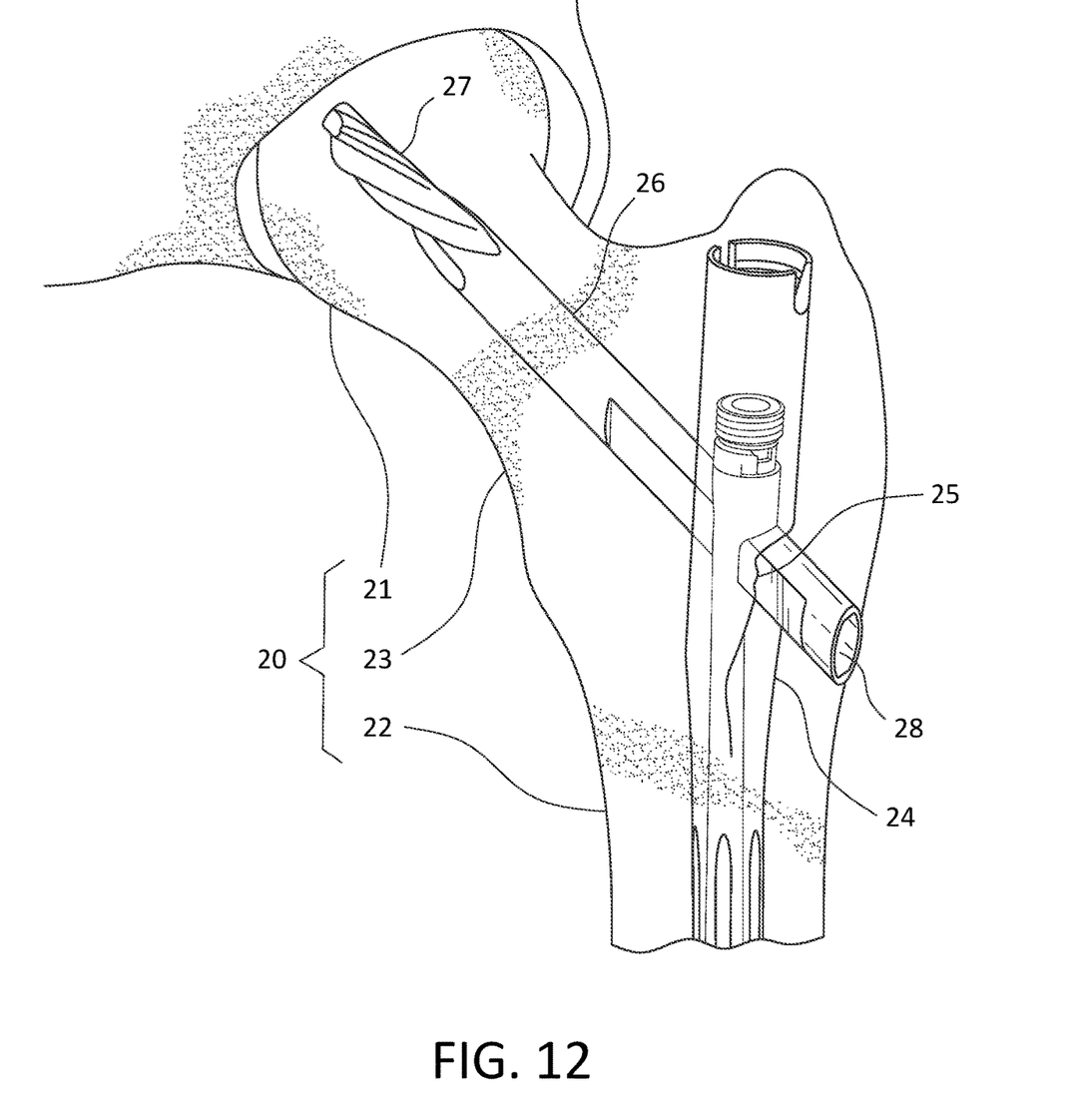
FIG. 12 shows an intramedullary nail and a helical blade positioned in a long bone.

A system for penetrating the lateral cortex of a long bone 20 as disclosed herein may be used for properly positioning lag screws or helical blades within an intramedullary nail, where the lag screw or blade passes through the axis of the intramedullary nail and anchors the intramedullary nail to the bony cortex of the long bone, preventing rotation of the intramedullary nail. The long bone 20 may be a femur as shown in FIG. 12, where the long bone 20 has a head 21, a shaft 22, and a neck 23 therebetween. In cases where the bone 20 is broken, it may become necessary to position an intramedullary nail 24 within the body 22 of the long bone 20. To prevent rotation of the nail 24, a lag screw 26 passes through an oblique hole 25 through nail 24, and anchors nail 24 to the surrounding bone of long bone 20. Lag screw 26 may include a spiral or helical cutting edge 27 to drill through bone, and a bore 28 configured to fit over a guidewire 3 (not shown in FIG. 12). Proper positioning of lag screw 26 relative to hole 25 through nail 24 is important, to prevent damaging nail 24 due to contact with lag screw 26 as lag screw 26 passes through hole 25.

Figure 13:
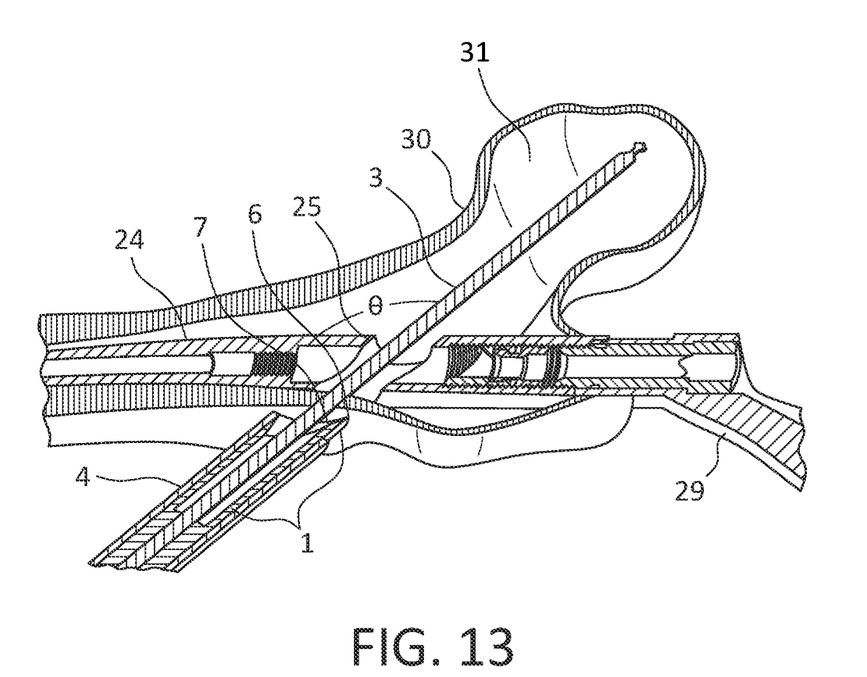
FIG. 13 shows use of a system of FIGS. 1 and 2 for penetrating the lateral cortex of a long bone having an intramedullary nail therein.

FIG. 13 shows installation of an intramedullary nail 24 within the body 22 of a femur, where the femur has a surface formed of cortical bone 30, and an interior 31 containing cancellous bone (not shown in FIG. 13). Installation may be carried out with the embodiment of FIG. 1. Intramedullary nail 24 is positioned in the shaft of the femur by methods known in the art, with insertion handle 29 being used to assist in positioning of nail 24. Nail 24 has oblique hole 25 passing through nail 24, where hole 25 has an axis at an angle θ. The system of FIG. 1 is used to insert a guidewire 3 through hole 25, along the axis of hole 25 as shown in FIG. 13.

In practice, a wire guide is placed within guide sleeve 4. Guide sleeve 4 is used to protect soft tissue, e.g., muscle or fascia, from damage caused by movement of a lag screw or helical blade as it passes through tissue. The distal end of guide sleeve 4, which may be referred to as a blade/screw guide sleeve, is positioned near the near the lateral cortex of a fractured femur. The guide wire 3 is advanced through the wire guide to a desired position within the femoral head. The wire guide is then extracted, and the tubular cortex penetrator 1 is advanced over the guide wire 3 to a position near lateral cortex bone. The distal end of tubular cortex penetrator 1 is advanced until the cutting edge 6 contacts the surface of the cortical bone 30. Cutting edge 6 is then used to cut into the surface of the cortical bone 30. In some embodiments, the tubular cortex penetrator is rotated about its axis within blade/screw guide sleeve 4, and the cutting edge 6 at the distal end of the tubular cortex penetrator 1 cuts completely through the lateral cortex of the femur upon rotation of the tubular cortex penetrator 1. Also, the tubular cortex penetrator may be rotated about its axis within blade/screw guide sleeve 4 to weaken the surface of the bone by forming a circular or oval score on the lateral cortex, and then the proximal end 11 of the penetrator 1 (not shown in FIG. 13) may receive an impact from a tool, so that the cutting edge 6 cuts through the lateral cortex along the circular or oval score upon transmission of an impact force from the proximal end 11.

Once an opening has been formed through the lateral cortex, the tubular cortex penetrator 1 is withdrawn from guide sleeve 4, while leaving guide wire 3 in place. A head element 26, i.e., a lag screw or helical blade, shown in FIG. 12, is then advanced through guide sleeve 4 along guide wire 3, and screwed into position in the neck 23 and head 21 of the femur, so that the head element 26 is advanced through hole 25 of nail 24, without nicking nail 24. Once the head element 26 has been screwed into position, the guide sleeve 4 and the guide wire 3 may be removed.

Figure 14:
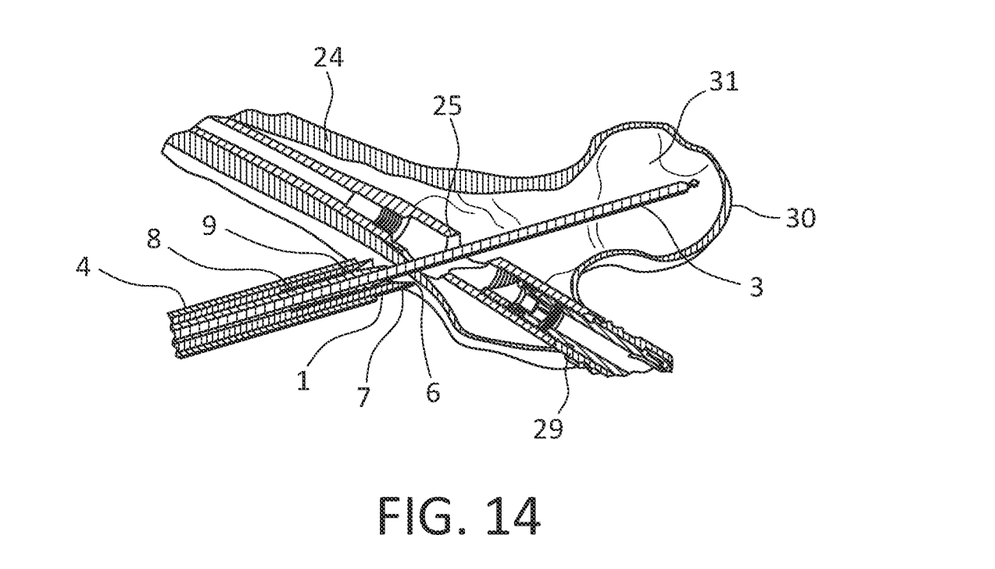
FIGS. 14 and 15 shows use of a system of FIGS. 5 and 6 for penetrating the lateral cortex of a long bone having an intramedullary nail therein.

FIG. 14 shows a second embodiment of installation of an intramedullary nail 24 within the body 22 of a femur, using the system of FIG. 5. The femur has a surface formed of cortical bone 30, and an interior 31 containing cancellous bone (not shown in FIG. 13). Intramedullary nail 24 is positioned in the shaft of the femur by methods known in the art, with insertion handle 29 being used to assist in positioning of nail 24. Nail 24 has oblique hole 25 passing therethrough, where hole 25 has an axis at an angle θ. The system of FIG. 5 is used to insert a guidewire 3 through hole 25, along the axis of hole 25 as shown in FIG. 13.

Figure 15:
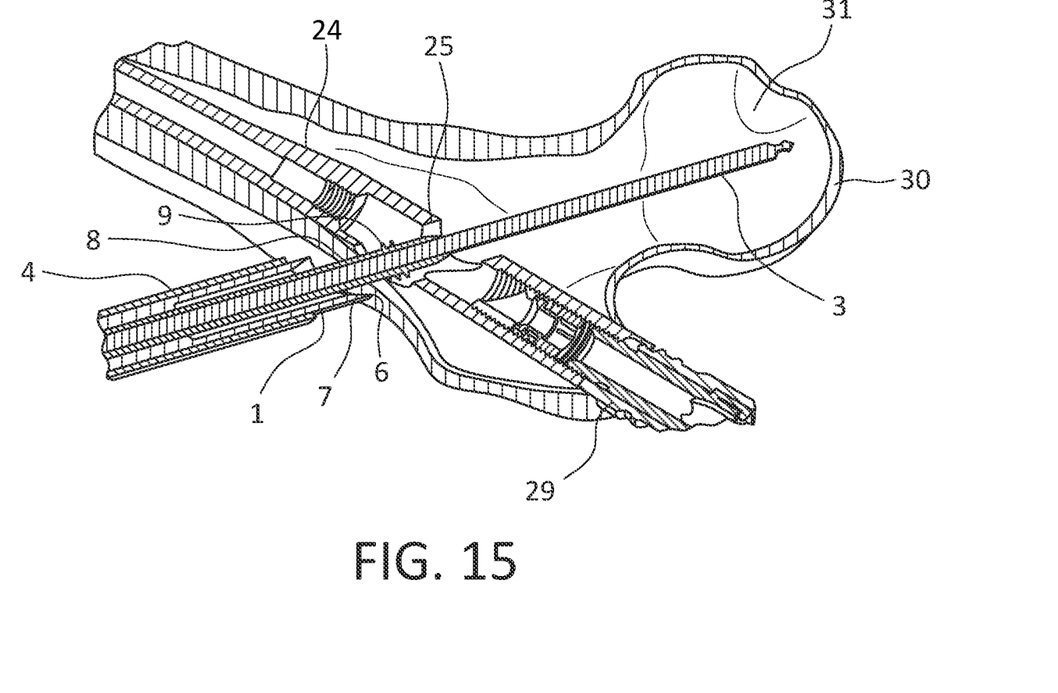

A wire guide is placed within guide sleeve 4, and the distal end of guide sleeve 4 is positioned near the near the lateral cortex of a fractured femur. The guide wire 3 is advanced through the wire guide to a desired position within the femoral head. The wire guide is then extracted, and hollow extraction screw 8 is advanced over the guide wire to a position near the lateral cortex bone. The tubular cortex penetrator 1 is then advanced over the guide wire 3 to a position near the lateral cortex bone, until the end of extraction screw 8 with threading 9 is positioned with the proximal end of a bore through penetrator 1, as seen in FIG. 14. As seen in FIG. 15, the hollow extraction screw 8 may then be advanced out of the bore of penetrator 1, and used to drill into or through the lateral cortex bone. The distal end of tubular cortex penetrator 1 is then advanced until the cutting edge 6 contacts the surface of the cortical bone 30, and used to cut into the surface of the cortical bone 30 as described above with regard to FIG. 13. After the penetrator cuts through cortical bone 30, the threaded end of extraction screw 8 may be withdrawn into the distal end of the bore of penetrator 1, and penetrator 1 and extraction screw 8 may be withdrawn along guidewire 3 while leaving guidewire 3 and guide sleeve 4 in place at the femur.

Figure 16:
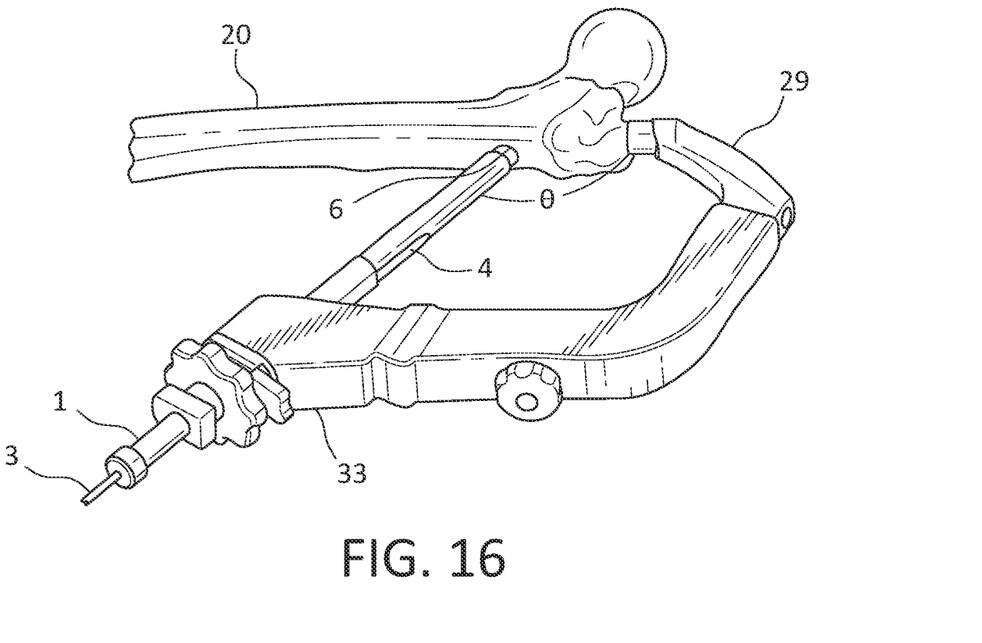
FIG. 16 show use of an aiming arm with a system for penetrating the lateral cortex of a long bone, including a tubular cortex penetrator.

FIG. 16 shows use of a handle 29 with an aiming arm 33 to control relative positioning of an intramedullary nail 24 and a tubular cortex penetrator 1. As shown in FIG. 13, an intramedullary nail 24 is positioned along the shaft of the femur. The proximal end of nail 24 is secured to handle 29, and held in a desired position for installation. Aiming arm 33 has a bore which receives blade/screw guide sleeve 4. The bore of aiming arm 33 allows blade/screw guide sleeve 4 to move axially toward the femur 20, or away from the femur 20. When the distal end of blade/screw guide sleeve 4 is in proximity to the cortical bone at the surface of femur 20, blade/screw guide sleeve 4 may be locked in position, and tubular cortex penetrator 1 and guidewire 3 may be advanced into blade/screw guide sleeve 4 until cutting edge 6 of penetrator 1 contacts the bone. Desirably, blade/screw guide sleeve 4 and nail 24 meet at an angle θ, where θ generally corresponds to an angle between the neck and the shaft of the femur.

Figure 17:
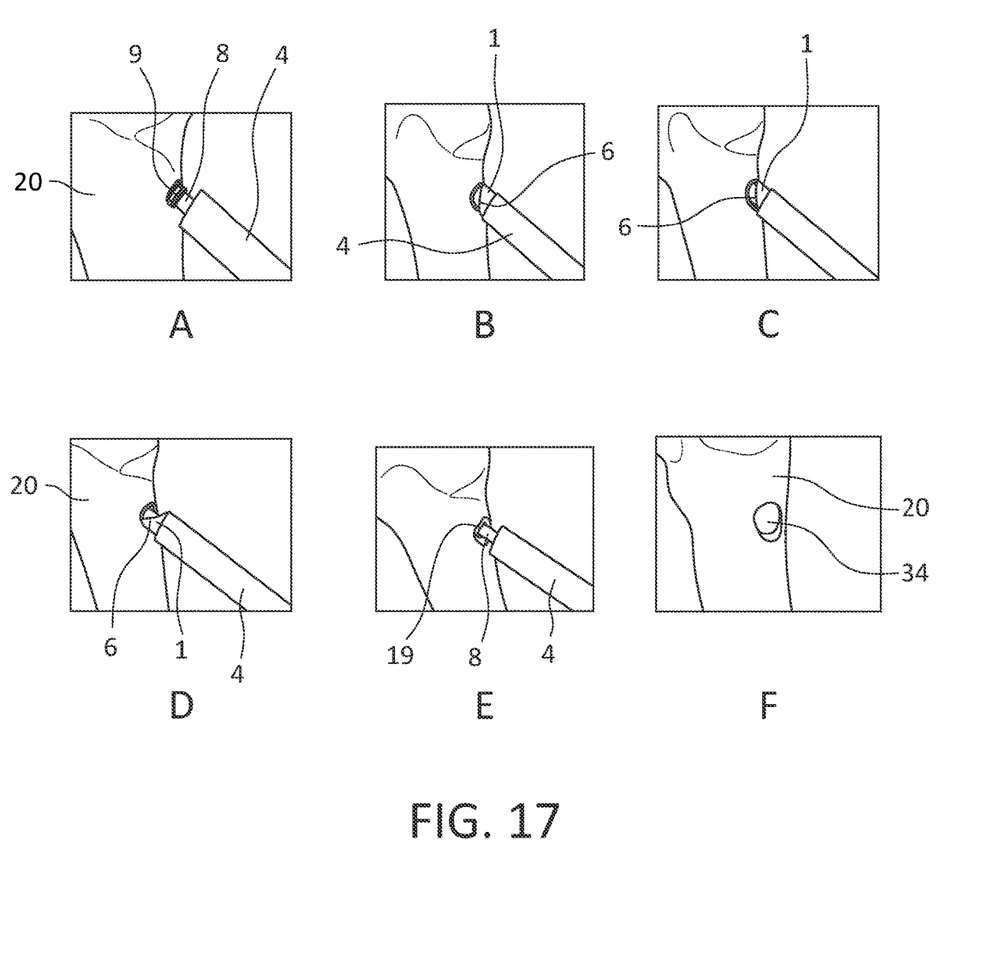
FIG. 17 shows use of a system of FIGS. 5 and 6 for penetrating the lateral cortex of a long bone.

FIG. 17 shows use of a system for penetrating the lateral cortex, in particular the embodiment of FIG. 5, illustrated on a femoral saw bone model. The distal end of guide sleeve 4 is advanced to the bone 20, e.g., the femur. A wire guide is advanced to the lateral cortex through the guide sleeve, and guide wire 3 is advanced through the wire guide and into the femoral head to a desired depth. The wire guide is then removed, and hollow extraction screw 8 is advanced to the lateral cortex over guide wire 3. Tubular cortex penetrator 1 is advanced through guide sleeve 4, over the hollow extraction screw 8, as shown in FIG. 17, panel A. Hollow extraction screw 8 is rotated about its axis to form a hole in the bone. As shown in FIG. 17, panel B, the tubular cortex penetrator 1 is advanced through the guide sleeve 4 until the cutting edge 6 of penetrator 1 contacts bone 20, with penetrator 1 surrounding hollow extraction screw 8. As seen in FIG. 17, panels C and D, tubular cortex penetrator 1 is then rotated about its axis until the cutting edge 6 of penetrator 1 scores the surface of bone 20. Rotation may be continued until cutting edge 6 of penetrator 1 cuts a disk of bone 19 away from femur 20, as shown in FIG. 17, panel E. Alternatively, an impact force applied to the proximal end of penetrator 1 may form a disk of bone 19 by causing the portion of bone 20 defined by the score to separate from the surrounding bone. Again referring to FIG. 17, panel E, penetrator 1 is withdrawn into guide sleeve 4, leaving a disk of bone 19 surrounding hollow extraction screw 8. In some embodiments, the most distal threads 9 on extraction screw 8 are buttressed against an inner surface of disk 19. The bone disk 19 may be pulled from the femur by withdrawing the threaded end of extraction screw 8 into a proximal end of the bore running through penetrator 1. As show in FIG. 17, panel F, withdrawal of guide sleeve 4 and hollow extraction screw 8, together with the guidewire 3, from the femur shows that use of the system described herein leaves bone 20 with a clean hole 34 through the lateral cortex of bone 20. In use for repairing a damaged bone, however, hollow extraction screw 8 and penetrator 1 will normally be withdrawn while leaving guidewire 3 (not shown in FIG. 15) and guide sleeve 4 in place. A lag screw or helical blade 26, as shown in FIG. 12, may then be advanced over guidewire 3 and through guide sleeve 4, and screwed into cancellous bone through a nail 24, as shown in FIG. 12.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A system for penetrating a lateral cortex of a bone, comprising:
    a guide wire;
    a tubular cortex penetrator configured to pass over the guide wire, the tubular cortex penetrator having an inner surface, an outer surface, and an axial bore therethrough, the tubular cortex penetrator comprising:
        a proximal end, and
        a distal end comprising a beveled cutting edge configured to penetrate the lateral cortex; and
    a hollow extraction screw with an axial bore, a proximal end, a distal end, and a threaded first cutting edge on an outer surface of the hollow extraction screw;
    wherein the guide wire is configured to pass through the axial bore of the hollow extraction screw; and
    the hollow extraction screw is configured to retract into a distal end of the axial bore of the tubular cortex penetrator.

2. The system of claim 1, further comprising a guide sleeve configured to surround the outer surface of the tubular cortex penetrator.

3. The system of claim 1, wherein at least a portion of the inner surface of the tubular cortex penetrator is constricted so as to prevent radial movement of the hollow extraction screw within the tubular cortex penetrator, while allowing axial movement of the hollow extraction screw.

4. The system of claim 1, wherein the proximal end of the tubular cortex penetrator is configured to receive an impact from a tool, and the cutting edge at the distal end of the tubular cortex penetrator is configured to penetrate the lateral cortex upon transmission of an impact force from the proximal end.

5. The system of claim 1, wherein the tubular cortex penetrator is configured to be rotated about an axis thereof, and the cutting edge at the distal end of the tubular cortex penetrator is configured to cut through the lateral cortex upon rotation of the tubular cortex penetrator.

6. The system of claim 1, wherein the cutting edge at the distal end of the tubular cortex penetrator is on the outer surface of the tubular cortex penetrator, and the inner surface of the tubular cortex penetrator is beveled.

7. The system of claim 1, wherein the cutting edge at the distal end of the tubular cortex penetrator is on the inner surface of the tubular cortex penetrator, and the outer surface of the tubular cortex penetrator is beveled.

8. The system of claim 1, wherein:
    the outer surface of the hollow extraction screw comprises a second cutting edge comprising at least one flute at a distal tip of the hollow extraction screw; and
    the threaded first cutting edge on the hollow extraction screw is proximal to the second cutting edge.

9. The system of claim 1, wherein the threaded first cutting edge is at a distal tip of the hollow extraction screw.

10. A method of penetrating the lateral cortex using the system of claim 1, comprising:
    introducing the guide wire to a surgical site near the lateral cortex;
    passing the hollow extraction screw over the guide wire to the surgical site;
    introducing the tubular cortex penetrator to the surgical site by passing the tubular cortex penetrator distally over the hollow extraction screw;
    drilling the hollow extraction screw into the lateral cortex;
    using the cutting edge at the distal end of the tubular cortex penetrator to cut a hole through the lateral cortex to form a disk of severed bone; and
    withdrawing the hollow extraction screw, the tubular cortex penetrator, and the disk of severed bone from the surgical site while leaving the guide wire in position.

11. The method of claim 10, further comprising:
    introducing a guide sleeve to the surgical site; and
    introducing the tubular cortex penetrator to the surgical site through the guide sleeve.

12. A system for perforating a cortical surface of a bone and extracting bone material from an interior of said bone to thereby create a passageway into the interior of the bone comprising:
    an exterior tubular member having an interior passage and a longitudinal axis having a distal and proximal end, the tubular member comprising a tapered cutting edge at its distal end configured to be advanced at least partially through an exterior surface of a bone;
    an extraction screw configured to be inserted through the interior passage of the outer tubular member and into an interior of a bone to assist in extracting bone material, the extraction screw including an interior passage and a longitudinal axis having a distal and proximal end, the distal end including a tapered tip and a plurality of threaded protrusions proximal to the tapered distal end; and
    a guide wire over which the extraction screw is advanceable.

13. The system of claim 12, wherein the tubular member is configured to be rotated about an axis thereof, and the cutting edge at the distal end of the tubular member is configured to cut through the lateral cortex upon rotation of the member.

14. The system of claim 12, wherein the cutting edge at the distal end of the tubular member is on an outer surface of the tubular member, and an inner surface of the member is beveled.

15. A method of penetrating a lateral cortex of a bone using a tubular cortex penetrator, wherein the tubular cortex penetrator comprises an inner surface and an outer surface, the tubular cortex penetrator further comprising:
- a proximal end, and
- a distal end comprising a beveled cutting edge configured to penetrate the lateral cortex;
  - wherein at least a portion of the inner surface of the tubular cortex penetrator is constricted, the method comprising:
- introducing a guide sleeve to a surgical site near the lateral cortex;
- introducing a guide wire to the surgical site through the guide sleeve;
- passing the tubular cortex penetrator through the guide sleeve over the guide wire, so that the cutting edge at the distal end of the tubular cortex penetrator exits the guide sleeve near the lateral cortex, wherein the constricted portion of the inner surface of the tubular cortex penetrator prevents radial movement of the guide wire relative to the tubular cortex penetrator, while allowing axial movement of the guide wire;
- using the cutting edge of the tubular cortex penetrator to penetrate the lateral cortex; and
- withdrawing the tubular cortex penetrator, while leaving the guide wire and guide sleeve in position.

\* \* \* \* \*